United States Patent
Warntjes

(10) Patent No.: US 12,140,655 B2
(45) Date of Patent: Nov. 12, 2024

(54) DYNAMIC MAGNETIC RESONANCE ANGIOGRAPHY METHOD AND SYSTEM

(71) Applicant: SyntheticMR AB (publ), Linköping (SE)

(72) Inventor: Marcel Warntjes, Linköping (SE)

(73) Assignee: SYNTHETICMR AB (PUBL), Linköping (SE)

( * ) Notice: Subject to any disclaimer, the term of this patent is extended or adjusted under 35 U.S.C. 154(b) by 921 days.

(21) Appl. No.: 16/849,365

(22) Filed: Apr. 15, 2020

(65) Prior Publication Data
US 2021/0325499 A1 Oct. 21, 2021

(51) Int. Cl.
| | |
|---|---|
| *G01R 33/563* | (2006.01) |
| *A61B 5/026* | (2006.01) |
| *A61B 5/055* | (2006.01) |
| *G01R 33/50* | (2006.01) |
| *G01R 33/54* | (2006.01) |
| *G01R 33/56* | (2006.01) |

(52) U.S. Cl.
CPC ........ *G01R 33/5635* (2013.01); *A61B 5/0263* (2013.01); *A61B 5/055* (2013.01); *G01R 33/50* (2013.01); *G01R 33/546* (2013.01); *G01R 33/5601* (2013.01)

(58) Field of Classification Search
CPC .. G01R 33/5635; G01R 33/50; G01R 33/546; G01R 33/5601; A61B 5/0263; A61B 5/055
See application file for complete search history.

(56) References Cited

U.S. PATENT DOCUMENTS

| | | | | |
|---|---|---|---|---|
| 7,715,900 | B2* | 5/2010 | Yarnykh | G01R 33/5607 324/309 |
| 2010/0198046 | A1* | 8/2010 | Takei | A61B 5/055 600/410 |
| 2012/0296193 | A1* | 11/2012 | Koktzoglou | A61B 5/02007 600/410 |
| 2013/0123611 | A1* | 5/2013 | Riederer | A61B 5/0263 600/419 |

(Continued)

OTHER PUBLICATIONS

Johnson, C., et al., "Three-Station Three-Dimensional Bolus-Chase MR Angiography with Real-time Fluoroscopic Tracking," Radiology. vol. 272(1), 2014. p. 241-251 (Year: 2014).*

(Continued)

*Primary Examiner* — Sean A Frith
(74) *Attorney, Agent, or Firm* — Getech Law LLC; Jun Ye

(57) ABSTRACT

A dynamic magnetic resonance angiography, MRA, method, comprising: acquiring, by an MR scanning device, a multi-contrast magnetic resonance, MR, sequence of a portion of a body; identifying, by a processing circuit, blood vessels of the portion by identifying blood of the portion based on predetermined characteristic of blood and the multi-contrast MR sequence; generating, by the processing circuit, a first MRA image frame and a second MRA image frame, based on the multi-contrast MR sequence, respectively visualising a first part and a second part of the identified blood vessels; generating, by the processing circuit, a dynamic MRA image for visualising a dynamic blood flow through a part of the portion, based on the first and second MRA image frame.

24 Claims, 4 Drawing Sheets

(56) References Cited

U.S. PATENT DOCUMENTS

| | | | | |
|---|---|---|---|---|
| 2014/0081123 A1* | 3/2014 | Korosec | ............... | A61B 5/055 |
| | | | | 600/413 |
| 2016/0033593 A1* | 2/2016 | Isoda | ................ | A61B 5/4325 |
| | | | | 324/318 |
| 2016/0313424 A1* | 10/2016 | Parrish | ................ | G01R 33/483 |
| 2020/0041595 A1* | 2/2020 | Flask | ................ | G01R 33/5608 |

OTHER PUBLICATIONS

Yu, S., et al., "Noncontrast dynamic MRA in intracranial arteriovenous malformation (AVM): comparison with time of flight (TOF) and digital subtraction angiography (DSA)," Magnetic Resonance Imaging. vol. 30, 2012. p. 869-877 (Year: 2012).*

Kvernby et al.; Simultaneous three-dimensional myocardial T1 and T2 mapping in one breath hold with 3D-QALAS; Journal of Cardiovascular Magnetic Resonance 2014.16:102; Published online: Dec. 20, 2014.

Hélène Raoult, MD, et al., Neuroradiology:Time-resolved Spin-labeled MR Anglography for Cerebral Arteriovenous Malformations; radiology.rsna.org; Radiology: vol. 271: No. 2—May 2014.

J.B.M. Warntjes, et al.; Rapid Magnetic Resonance Quantification on the Brain: Optimization for Clinical Usage, Optimization of Rapid MR Quantification; Magnetic Resonance in Medicine 60:320-329 (2008).

Stuart A. Bobman et al.; Cerebral Magnetic Resonance Image Synthesis; © American Roentgen Ray Society: AJNR 6:265-269, Mar./Apr. 1985 0195-6108/85/0602-0265.

* cited by examiner

DYNAMIC MAGNETIC RESONANCE ANGIOGRAPHY METHOD AND SYSTEM

TECHNICAL FIELD

The present document relates to a dynamic magnetic resonance angiography, MRA, method and system for visualising a dynamic blood flow through a part of a portion, without using any contrast agents.

BACKGROUND

Magnetic resonance angiography (MRA) is widely used for imaging blood vessels, including arteries and veins, based on magnetic resonance imaging (MRI) techniques. Nowadays, the MRA is an important clinical tool for depicting positions, sizes and abundances of blood vessels of patients, which may be used to evaluate the blood vessels and to detect vessel abnormalities, such as malformations or aneurysms.

A typical MRI scanner comprises a large, powerful magnet, and can send signals to, e.g., a body portion of a patient. The returning signals can be detected and converted into images of the body portion by a computer device. The images can be obtained in multiple planes (axial, sagittal, coronal, or oblique) without repositioning the patient.

The MRI techniques are generally based on relaxation properties of excited hydrogen nuclei (protons) of an object under test. When the object to be imaged is placed in a powerful, uniform magnetic field of the MRI scanner, the spins of the atomic nuclei of water in the object with non-integer spin numbers within the object all align either parallel or anti-parallel to the magnetic field. From an MR acquisition, several physical properties of the object under test can be determined with an absolute scale. And an image can be reconstructed based on an acquired magnetic resonance sequence generated with the excitation.

Proton density (PD) refers to a concentration of protons in a tissue, wherein the protons are the hydrogen nuclei that resonates and gives rise to the nuclear magnetic resonance signal. Since most visible tissue protons are resident in water, it is often seen as looking at a water content. The proton density PD of a tissue usually refers to the concentration of protons in the tissue, relative to that in the same volume of water at the same temperature.

In order to understand the MRI techniques, it is important to understand the following time constants involved in the relaxation processes, which establish equilibrium following RF excitation. A nuclear magnetic resonance signal is attenuated due to two simultaneous relaxation processes. The loss of coherence of the spin system attenuates the signal with a time constant called a transverse relaxation time (T2). Concurrently, the magnetization vector slowly relaxes towards its equilibrium orientation that is parallel to the magnetic field by a time constant called longitudinal relaxation time (T1). A longitudinal relaxation rate R1 is a reciprocal of the longitudinal relaxation time T1 (R1=1/T1). A transverse relaxation rate R2 is a reciprocal of the transverse relaxation time T2 (R2=1/T2). The relaxation times T1 and T2 are typically measured in milliseconds (ms) or seconds (s). The corresponding relaxation rates R1 and R2 are therefore measured in units of $ms^{-1}$ or $s^{-1}$.

Normally, an acquired MRI sequence can result in images of the same anatomical section under different contrasts, such as T1, T2, and PD weighted images. The MRI techniques relies on differences in relaxation properties and proton density of the imaged tissue to display the different tissues with contrast, e.g., in different signal intensities or different colours, in the resulted MRI images. The contrast in MR images originates from the fact that different tissues have, in general, different R1 and R2 relaxation rates, and different PD. For example, Warntjes et al. *Magn Reson Med.* 2008; 60:320-9 teaches that these physical properties, e.g., R1 and R2 relaxation rates and PD, can be acquired by performing a single MR acquisition, to provide quantitative values of the imaged portion.

Time-of-flight (TOF) MRA is one of the most well-known method for obtaining MRA images, which is described in, e.g., Raoult et al. *Radiology.* 2014; volume 271:524-533. In short, stationary tissues of an imaged portion of a body, i.e. the imaged volume, become magnetically saturated by multiple repetitive RF-pulses that drive down their steady-state magnetization levels. Then, the "fresh" blood which has not experienced these RF-pulses, also known as unsaturated blood, flowing into the imaged portion, would have a higher initial magnetization comparing to the stationary tissues of the imaged portion. Thus, the signals representing the inflowing blood would appear "brighter" compared to its surrounding tissues of the imaged portion in the resulted MRA image. However, conventional MRA provides inadequate visualisation of the dynamic features (e.g., velocities, flow direction, turbulence) of blood flows.

With administration of contrast agents, e.g., gadolinium-based contrast agents which can shorten the T1 relaxation time of blood and render blood vessels bright in the MRA images, dynamic features of blood flows can also be observed with the MRI technologies. Such dynamic MRA images can be generated by performing e.g., a rapid succession of identical MR acquisitions.

However, adverse reactions, e.g., allergies, ranging from mild to severe caused by administration of contrast agents do occur.

Thus, there is a need to provide a method and system for providing a visualisation of the dynamic features of blood flows without administration of any contrast agents.

SUMMARY

It is an object of the present disclosure, to provide a new dynamic magnetic resonance angiography method and system for visualising a dynamic blood flow through a part of an imaged portion, which eliminates or alleviates at least some of the disadvantages of the prior art.

The invention is defined by the appended independent claims. Embodiments are set forth in the appended dependent claims, and in the following description and drawings.

According to a first aspect, there is provided a dynamic magnetic resonance angiography, MRA, method, comprising: acquiring, by an MR scanning device, a multi-contrast magnetic resonance, MR, sequence of a portion of a body; identifying, by a processing circuit, blood vessels of the portion by identifying blood of the portion based on predetermined characteristic of blood and the multi-contrast MR sequence; generating, by the processing circuit, a first MRA image frame and a second MRA image frame, based on the multi-contrast MR sequence, respectively visualising a first part and a second part of the identified blood vessels; generating, by the processing circuit, a dynamic MRA image for visualising a dynamic blood flow through a part of the portion, based on the first and second MRA image frame.

The dynamic blood flowing through a part of the portion may be visualised based on a single multi-contrast MR acquisition, without administration of any contrast agents. Thus, the safety of the patients can be improved by reducing the risks of adverse reactions caused by the administration of contrast agents. The time of measurement can be reduced as only a single multi-contrast MR acquisition is needed for generating the dynamic MRA image.

The multi-contrast MR sequence refers to a MR sequence acquired by performing a multi-contrast MR acquisition. The multi-contrast MR sequence may be acquired by a single multi-contrast MR acquisition, which may acquire information of the imaged portion for generating multiple MRI images with particular appearances. Consequently, a plurality of multi-contrast images may be resulted from the single multi-contrast MR acquisition.

For examples, the multi-contrast MR sequences may be an inversion-delay Gradient-Echo (GE) acquisition or a multi-echo Fast-Spin Echo (FSE) acquisition. In an inversion-delay GE acquisition, the magnetization of the spins is inverted and subsequently measured using a continuous, small flip-angle read-out. The continuous measurement is usually split into several consecutive images, with an increasing delay time per image. The signal intensities in these images will be a function of R1 relaxation rate of the tissues. The multi-echo FSE acquisition is a single acquisition that can generate images at various echo times. The signal intensities in these images will be a function of R2 relaxation rate of the tissues.

Different techniques may be combined such that the multi-contrast MR sequence, e.g., a QALAS sequence described in Kvernby et al, *Journal of Cardiovascular Magnetic Resonance.* 2014 Dec. 20; 16:102, may generate images of signal intensities affected by both R1 and R2 relaxation rate.

The method may further comprise: generating a plurality of multi-contrast images based on the multi-contrast MR sequence; identifying the blood vessels of the portion by identifying the blood of the portion based on the predetermined characteristic of blood and the plurality of multi-contrast images; wherein the multi-contrast MR sequence comprises quantification information of the portion; wherein the quantification information of the portion comprises a longitudinal relaxation rate R1, and a transverse relaxation rate R2; and wherein the predetermined characteristic of blood comprises: a value of a longitudinal relaxation rate R1 of blood, and a value of a transverse relaxation rate R2 of blood.

The step of acquiring the multi-contrast MR sequence and the step of generating the plurality of multi-contrast images may be one step instead of two. It is common that a MR scanner may perform an acquisition and result in a plurality of images with different contrasts.

The step of identifying blood vessels may comprise: calculating quantification values of each voxel of a plurality of voxels representing the portion, based on the plurality of multi-contrast images; wherein each voxel of the plurality of voxels corresponds to a volume of the portion, and wherein the quantification values comprise: a value of a longitudinal relaxation rate R1 and a value of a transverse relaxation rate R2; selecting a first group of voxels of the plurality of voxels representing the identified blood vessels, by comparing the quantification values of each voxel with the predetermined characteristic of blood.

The quantification values for each voxel, including the R1, R2 and even PD, may be calculated in different known ways. For example, the R1 and R2 values may be calculated by generating R1 and R2 maps, respectively. When the quantification values comprise additional parameters, e.g., a PD value, additional maps, e.g., a PD map, may be generated. The R1, R2 and PD maps describe the signal behaviour of the multi-contrast images resulted from the multi-contrast MR sequence.

At least two multi-contrast images are needed for generating each of the above-mentioned maps. Thus, a plurality of multi-contrast images is needed to generate the R1, R2 and PD maps.

A voxel is a volume element, used to represent a tiny three-dimensional (3D) portion in a 3D volume. Voxels are frequently used in the visualization and analysis of medical 3D images. Here, each voxel represents a corresponding tiny volume of the imaged portion. Thus, each voxel has a plurality of quantification values, e.g., R1 and R2, representing characteristics of the tissues of the corresponding tiny volume of the imaged portion.

A pixel is an element, used to represent a tiny 2D portion in a 2D image. The 3D imaged portion may be sliced into a stack of slices each having a thickness. A voxel may be considered to correspond to a pixel for a given slice thickness. In other words, a voxel can be considered as a volumetric pixel for the given slice thickness. Thus, a 3D image may be converted into a series of 2D images. Consequently, the 3D voxels may be converted into a series of 2D pixels.

These quantification values of the voxel may be used to determine the tissues of the tiny volume represented by the voxel. If the quantification values of a voxel, e.g., R1 and R2, equal to the predetermined R1 and R2 values of blood, respectively, or fall within the range of the predetermined R1 and R2 values of blood, respectively, this voxel can be identified as a part of the blood or blood vessels. Consequently, the tiny volume of the imaged portion represented by this voxel can also be identified as a part of the blood or the blood vessels.

The step of generating a first MRA image frame may comprise: determining a first group of values corresponding to the first part of the identified blood vessel to be visualised in the first MRA image frame, wherein the first group of values comprise a value of longitudinal relaxation rate R1 and a value of transverse relaxation rate R2; selecting a second group of voxels of the plurality of voxels representing the first part of the identified blood vessel by comparing the quantification values of each voxel with the first groups of values; generating the first MRA image frame visualising the first part of the identified blood vessels, based on the second group of voxels.

The MRA image frame can be generated by a masking step. Masking technique is known for separating a part of an image from its surroundings in the image based on certain criteria.

The masking step may comprise creating a mask which covers a part of the image based on the criteria, and treating this part and its surroundings in the image differently.

For example, the values of the relaxation rates R1 and R2 can be used as criteria to separate the first part of the identified blood vessels from its surrounding tissues. Then the selected second group of voxels may be "masked" and treated differently from other voxels.

The masked voxels and the unmasked voxels can be treated differently in many different ways, such as changing the brightness and/or the colour of the voxels. For example, the MRA image frame may be generated by keeping the brightness of the masked voxels, i.e. the selected second group of voxels, unchanged, while suppressing the brightness of the other voxels. Alternatively, the MRA image frame may be generated by increasing the brightness of the masked voxels, while keeping the brightness of the other voxels unchanged.

The quantification information of the portion may comprise a Proton Density, PD; wherein the predetermined characteristic of blood comprises: a value of a PD of blood; preferably the value of the PD of blood is in a range of 90%-140%, more preferably in a range of 92%-120%, most preferably in a range of 95%-100%.

Since the blood is similar to pure water, the value of the PD of blood is typical 95%-100%.

However, inflow of "fresh" blood comprising unsaturated spins into the imaged portion may lead to a higher signal intensity than expected. This may result in a PD values higher than 100%.

The quantification values of each voxel may comprise: a value of a PD.

The first group of values may comprise: a value of a PD.

By comparing the quantification values of a voxel with the predetermined values of R1 and R2 of blood, it is possible to identify the blood vessels from other tissues. Additionally, by comparing also the PD value of each voxel with the predetermined PD value of blood, a more accurate identification of the blood or blood vessels can be achieved.

The step of identifying blood vessels may comprise: selecting a part of the multi-contrast MR sequence representing the identified blood vessels, based on the predetermined characteristic of blood; wherein the predetermined characteristic of blood comprises: a representation of a signal intensity of blood.

Alternatively, it is possible to recognise blood directly from the raw data, i.e. the multi-contrast MR sequence, without analysing the plurality of multi-contrast images. The acquired multi-contrast MR sequence has already defined the characteristics of different tissues, including the blood, in terms of signal behaviours of the plurality of multi-contrast images, e.g., signal intensities in the images. For example, one tissue may be bright in one image, and it may be dark in another image. The quantification information, e.g., R1, R2 and PD, is merely an objective description of the signal behaviours in the images. Therefore, it is not necessary to generate the plurality of multi-contrast images and calculate the quantification values for identifying the blood vessels of the portion, as the multi-contrast MR sequence itself simply comprises all the information of the plurality of multi-contrast images.

Based on an adequate information of the expected signal intensity of blood, it is possible to select the part of the multi-contrast MR sequence representing the identified blood vessels directly, without analysing the multi-contrast images.

The step of generating a first MRA image frame may comprise: selecting a first group of data of the selected part of the multi-contrast MR sequence corresponding to the first part of the identified blood vessel; generating the first MRA image frame visualising the first part of the identified blood vessels, based on the multi-contrast MR sequence and the first group of data.

The step of generating a first and a second MRA image frame may comprise: visualising the first MRA image frame and the second MRA image frame, by a Maximum Intensity Projection, MIP.

The step of generating a first and a second MRA image frame may comprise visualising the first MRA image frame and the second MRA image frame, by a Minimum Intensity Projection, MinIP.

Even though the MRA image frame may visualise 3D slices that contain the entire identified blood vessels of interest, it is more common to display the 3D information on a 2D display, such as a computer monitor, by a Maximum Intensity Projection (MIP) or a Minimum Intensity Projection (MinIP). A 2D image of a selected volume may be generated where each pixel is represented by displaying the maximum or minimum intensity in each voxel.

MIP is a method for visualising 3D data that projects in a visualisation plane the voxels with a maximum intensity. In other words, projection lines are projected over a plane through a portion of a body, and the maximum intensity of each projection line is identified and visualised.

MinIP is a method for visualising 3D data that projects in a visualisation plane the voxels with a minimum intensity. Consequently, MinIP imaging can visualise structures with a low intensity in an imaged volume. In other words, the MinIP projection lines are projected over a plane through a portion of a body, and the minimum intensity of each projection line is identified and visualised.

By MIP imaging, the resulting MRA images resemble conventional catheter angiography images. That is, the identified blood vessels look brighter (e.g., in white colour) and other tissues look darker (e.g., in black colour) in the resulted MRA image.

By MinIP imaging, the resulting MRA images appear as reversed images of the resulting MRA images. That is, the identified blood vessels look darker (e.g., in black colour), and other tissues look brighter (e.g., in white colour) in the resulted MRA image.

The step of generating a first and a second MRA image frame may comprise: generating a synthetic MR image representing the portion based on the multi-contrast MR sequence, as a static background image of the dynamic MRA image; generating the dynamic MRA image based on the first, the second MRA image frame, and the synthetic MR image.

The synthetic MR image may be generated based on the, e.g., the same R1, R2 and PD maps using signal calculation of the image intensity based on the R1, R2 and PD values of the voxels. The concept of synthetic MR imaging is well-known in the field, see e.g. "*Cerebral Magnetic Resonance Image Synthesis*", Bobman et al. *Am J NeuroRadiol* 1985; 6:265-269.

The synthetic MR image may function as a static background reference image illustrating the whole imaged portion, e.g., the head and/or the neck.

Thus, comparing to a traditional MRA image having a black background wherein only the identified blood vessels are visible, the synthetic MR image may present a better anatomical image, which can facilitate the recognition of the relative positions and sizes of the identified blood vessels.

The identified blood vessels can be either added or subtracted from the synthetic MR image, resulting in either bright or dark blood vessels in the dynamic MRA image, respectively.

One example of the synthetic MR image may be a synthetic T1 relaxation time weighted, T1W, image.

The first part and the second part of the identified blood vessels may be at least partially overlapping or nonoverlapping.

The first part of the identified blood vessels may comprise early inflow arteries of the identified blood vessels, and the second part of the identified blood vessels comprises late inflow arteries of the identified blood vessels.

The early and late inflow arteries of the identified blood vessels respectively refer to the part of the arteries of the imaged portion which the blood inflows earlier and the part of the arteries of the imaged portion which the blood inflows later. That is, the unsaturated "fresh" blood flows through the early inflow arteries firstly, and then flows through the late inflow arteries of the imaged portion.

Since the measured values of R1 and R2 of the blood are different when it is in the early inflow arteries and when it is in the late inflow arteries, it is possible to separate the early and late inflow arteries of the identified blood vessels, such that a dynamic blood flow from the early inflow arteries to the late inflow arteries can be visualised by a single multi-contrast MR acquisition.

The first part of the identified blood vessels may comprise arteries of the identified blood vessels.

The second part of the identified blood vessels may comprise all the identified blood vessels, or veins of the identified blood vessels.

The dynamic MRA image may consecutively display the first and second MRA image frame.

A dynamic image may be generated based on a plurality of frames in many different ways.

For example, since both the first and second MRA image frame are generated based on the same multi-contrast MR sequence, the major differences between these two MRA image frames should be the first and second part of the identified blood vessels they respectively visualise. By consecutively displaying the first and second MRA image, the dynamic MRA image may appear as a dynamic image, or as a short video clip, to visualise the dynamic blood flow from the first to the second part of the identified blood vessels, or vice versa.

At least a first portion of the first MRA image frame and a second portion of the second MRA image frame may be displayed in different colours or different brightnesses.

The method may further comprise: generating at least a third MRA image frame visualising at least a third part of the identified blood vessels; generating the dynamic MRA image based on the first, second and at least the third MRA image frame, wherein the first part, second part and at least the third part of the identified blood vessels are at least partially overlapping or nonoverlapping.

The second, third, and any number of additional MRA image frames may be generated in a similar way as the first MRA image frame. The visualisation of the dynamic blood flow may be achieved by displaying a rapid succession of sequential MRA image frames.

A serial of MRA image frames each covering a small part of the identified blood vessels may visualise the dynamic features of blood flows with an improved accuracy. This may facilitate the analysis of the blood vessels.

The value of the longitudinal relaxation rate R1 of blood may be in a range of 0.4-0.6 $s^{-1}$; and the value of transverse relaxation rate R2 of blood may be in a range of 20-30 $s^{-1}$.

The portion of the body may comprise a head and/or a neck.

Each voxel of the plurality of voxels may have an intensity value, wherein the method may further comprise: calculating a perfusion value by summing the intensity value of each voxel of the first group of voxels.

The term "intensity", also known as "signal intensity", in the field of MR refers to a shade of grey of a tissue or of a voxel representing the tissue in an MRI image. Generally, a high intensity means it would look "white" in the MRI image, an intermediate intensity means it would look "grey" in the MRI image, and a low intensity means it would look "black" in the MRI image.

A perfusion is known as a delivery of blood to a capillary system in a tissue. The perfusion is normally measured as a rate at which the blood is delivered to the tissue at a unit of $m^3/(s \cdot kg)$. Thus, the perfusion is important for assessing a patient's condition, e.g., in case of strokes, plaques or vessel constrictions.

The sum of the intensities of the voxels representing the identified blood vessels is proportional to a total amount of blood that entered the imaged portion during acquisition. Thus, the sum of the intensities, i.e. the calculated perfusion value, may be considered as a measure for perfusion of the patient. The higher the calculated perfusion value, the higher the perfusion. The lower the calculated perfusion value, the lower the perfusion.

It is advantageous to provide an estimation of the perfusion based on the multi-contrast MR sequence.

Each voxel of the plurality of voxels may have an intensity value, wherein the method may further comprise: calculating a first sum by summing intensity values of voxels of the plurality of voxels representing the first part of the identified blood vessels; calculating a second sum by summing intensity values of voxels of the plurality of voxels representing the second part of the identified blood vessels; calculating a rate of change of the first sum and second sum as a measure of a mean transit time of blood through the portion of the body.

Mean Transit Time (MU) of blood is known as an average time, normally in seconds, that the blood spends within a determinate volume of capillary circulation.

Since the sum of the intensities of a part of the identified blood vessels is proportional to a total amount of blood that entered this part, a rate of change of the sums over the different parts of the blood vessels may indicate how fast the blood enters and/or leaves the imaged portion. Thus, the rate of change of the sums may be considered to be proportional to the mean transit time. The faster the sum increases, the shorter the mean transit time. The slower the sum increases, the longer the mean transit time.

It is advantageous to provide an estimation of the mean transit time based on the multi-contrast MR sequence.

According to a second aspect, there is provided a dynamic magnetic resonance angiography, MRA, system, comprising: an MR scanning device configured to: acquire a multi-contrast magnetic resonance, MR, sequence of a portion of a body; and a processing circuit configured to: identify blood vessels of the portion by identifying blood of the portion based on predetermined characteristic of blood and the multi-contrast MR sequence; generate a first MRA image frame and a second MRA image frame, based on the multi-contrast MR sequence, respectively visualising a first part and a second part of the identified blood vessels; generate a dynamic MRA image for visualising a dynamic blood flow through a part of the portion, based on the first and second MRA image frame.

The system may further comprise a user interface configured to display the dynamic MRA image.

According to a third aspect, there is provided a non-transitory computer readable recording medium having computer readable program code recorded thereon which when executed on a device having processing capability is configured to perform the method of the first aspect.

DESCRIPTION OF EMBODIMENTS

The present invention will now be described more fully hereinafter with reference to the accompanying drawings, in which currently preferred embodiments of the invention are shown.

Figure 7:
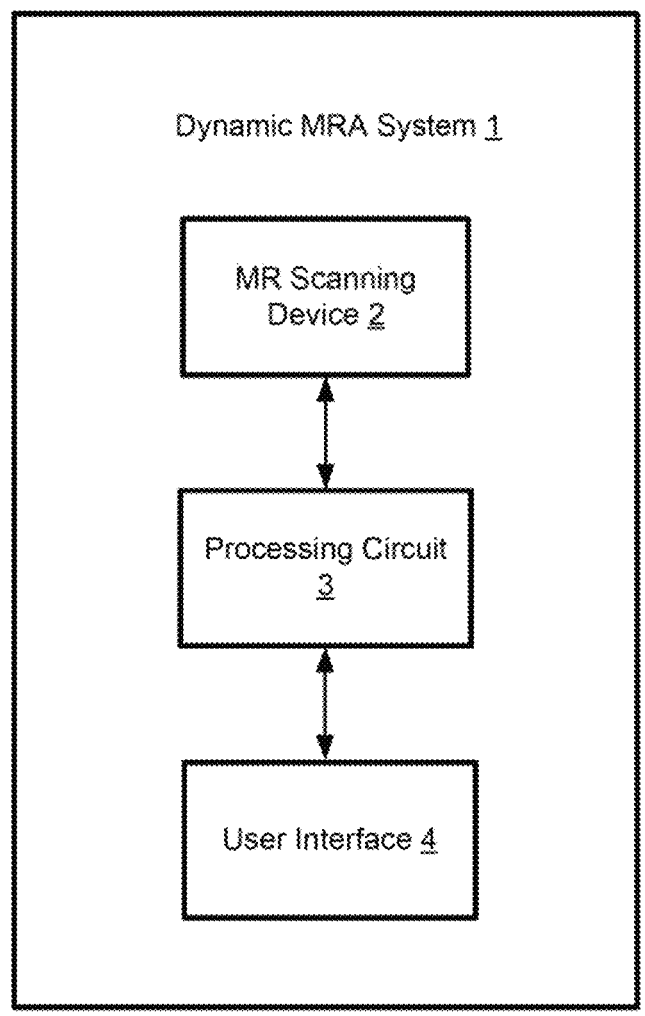
FIG. 7 is an example of a schematic block diagram of a dynamic MRA system.

In connection with FIG. 7, the dynamic MRA system 1 will be discussed in more detail. The dynamic MRA system 1 comprises an MR scanning device 2 and a processing circuit 3.

The MR scanning device 2 is configured to acquire a multi-contrast MR sequence of a portion of a body. The multi-contrast MR sequence may comprise quantification information of the portion, which may include a longitudinal relaxation rate R1, and a transverse relaxation rate R2, of tissues of the portion.

The processing circuit 3 is configured to carry out overall control of functions and operations of the dynamic MRA system 1. The processing circuit 3 may include a processor, such as a central processing unit (CPU), microcontroller, or microprocessor. The dynamic MRA system 1 may comprise a memory. The processing circuit 3 may be configured to execute program codes stored in the memory, in order to carry out functions and operations of the dynamic MRA system 1.

The memory may be one or more of a buffer, a flash memory, a hard drive, a removable medium, a volatile memory, a non-volatile memory, a random access memory (RAM), or another suitable device. In a typical arrangement, the memory may include a non-volatile memory for long term data storage and a volatile memory that functions as system memory for the dynamic MRA system 1. The memory may exchange data with the processing circuit over a data bus. Accompanying control lines and an address bus between the memory and the processing circuit also may be present.

Functions and operations of the dynamic MRA system 1 may be embodied in the form of executable logic routines (e.g., lines of code, software programs, etc.) that are stored on a non-transitory computer readable medium (e.g., the memory) of the dynamic MRA system 1 and are executed by the processing circuit 3. Furthermore, the functions and operations of the dynamic MRA system 1 may be a stand-alone software application or form a part of a software application that carries out additional tasks related to the dynamic MRA system 1. The described functions and operations may be considered a method that the corresponding device is configured to carry out. Also, while the described functions and operations may be implemented in software, such functionality may as well be carried out via dedicated hardware or firmware, or some combination of hardware, firmware and/or software.

The dynamic MRA system 1 may comprise a user interface 4. The user interface 4 may be configured to output data and information, e.g., the dynamic MRA image for visualising a dynamic blood flow through a part of the portion, and/or the first and second MRA image frame. The user interface 4 may be configured to receive data and information, such as a command, from one or several input devices. The input device may be a computer mouse, a keyboard, a track ball, a touch screen, or any other input device. The user interface 4 may send the received data and information to the processing circuit 3 for further processing.

In connection with FIG. 1, the R1 and R2 relaxation rate for the blood will be discussed in more detail.

It is known that blood has its own characteristics. For example, blood has a specific range of R1, R2 and PD values. R1 of the blood is typical 0.4-0.6 $s^{-1}$, R2 of the blood is typical 20-30 $s^{-1}$. PD of the blood is similar to pure water, which is typical 95%-100%. However, inflow of "fresh" blood comprising unsaturated spins into the imaged portion may lead to a higher signal intensity than expected. This may result in PD values higher than 100%, e.g., 140%.

Thus, by using these known characteristics of blood, e.g., a combination of R1 and R2 of the blood, or preferably a combination of R1, R2 and PD of the blood, it is possible to separate the blood of the imaged portion from other tissues. Consequently, the blood vessels that the blood flows through can also be identified.

Figure 1:
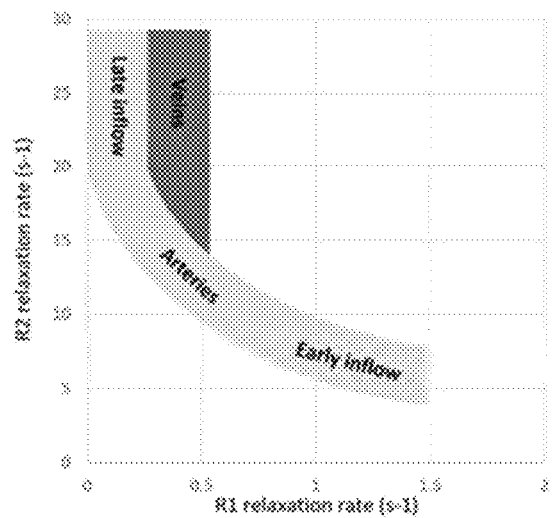
FIG. 1 is a plot showing R1 and R2 relaxation rate of blood.

The x-axis of FIG. 1 is the R1 relaxation rate ($s^{-1}$), and the y-axis of FIG. 1 is the R2 relaxation rate ($s^{-1}$). The grey areas of FIG. 1 comprise combinations of R1, R2 values, which may be used to separate the blood vessels from its surrounding tissues.

Continuous addition of unsaturated magnetization, i.e. "fresh" blood flowing into the imaged portion, will affect the signal intensity of each of the measurement points of the acquired MR sequence, disturbing the observation in comparison to a static situation, i.e. when there is no inflow of blood into the imaged portion. That is, inflow of "fresh" blood into the imaged portion of body during acquiring one multi-contrast MR sequence will cause changes of the observed R1, R2 and PD values.

For example, for a multi-echo MR acquisition, typically the signal intensity decreases as a function of an echo time. The reduced signal intensity can be expressed as an R2 relaxation rate, wherein a faster decrease corresponds to a higher R2 value. The inflow of blood, however, will cause a relative increasement of signal intensity at later echo times, resulting in an apparently lower R2 relaxation rate.

Similarly, signal increasement after an inversion pulse can be expressed as an R1 relaxation rate, wherein a faster increasement corresponds to a higher R1 value. The inflow of blood shortly after the inversion pulse will result in an early rise of signal intensity, causing an apparently higher R1 relaxation rate. While the inflow of blood at some time after the inversion pulse will result in a later rise of signal intensity, causing an apparently lower R1 relaxation rate. In both cases the PD will be higher owing to the additional signal intensity.

Consequently, the R1 and R2 values alone can be used to separate the blood of the arteries from the blood of the veins, and even the early inflow blood from the late inflow blood of the arteries. Consequently, the early and late inflow arteries of the imaged portion may be saparated. Together with PD values, a more accurate identification may be achieved.

The early and late inflow arteries of the identified blood vessels respectively refer to the part of the arteries of the imaged portion which the blood inflows earlier and the part of the arteries of the imaged portion which the blood inflows later. That is, the unsaturated "fresh" blood flows through the early inflow arteries firstly, and then flows through the late inflow arteries of the imaged portion.

Since the measured values of R1 and R2 of the blood are different when it is in the early inflow arteries and when it is in the late inflow arteries, it is possible to separate the early and late inflow arteries of the identified blood vessels, such that a dynamic blood flow from the early inflow arteries to the late inflow arteries can be visualised based on a single multi-contrast MR acquisition.

Further, due to the intrinsic differences between the blood flowing within arteries and veins, e.g., different blood oxygen levels, and different blood flow velocities, the blood flowing within arteries and veins has different R1 and R2 values. Thus, it is possible to separate arteries and veins based on the R1 and R2 values.

The combinations of R1 and R2 values of the blood of the early inflow arteries are at a high R1/low R2 end in FIG. 1. The combinations of R1 and R2 values of the blood of the late inflow arteries are at a low R1/high R2 end in FIG. 1

The blood of the veins has similar R2 values to the blood of the late inflow arteries, but has larger R1 values than the blood of the late inflow arteries in FIG. 1.

The relative changes of R1, R2 and PD values of blood due to inflow of unsaturated blood, in comparison to the values observed in the absence of inflow, extends the ranges of R1, R2 and PD values of predetermined characteristics of blood. Simultaneously this also allows for the creation of a dynamic MRA image. For example, firstly all blood vessels may be segmented in the MRA image, but then the segmented MRA image may be masked by using the known R1, R2 and PD values for the blood of the early inflow arteries, such that only the early inflow arteries are visualised. Subsequently, the segmented MRA image may be masked by using the known R1, R2 and PD values for the blood of the later inflow arteries, and for the blood of the veins, such that only the late inflow arteries and the veins are visualised, respectively. That is, by changing the R1, R2 and PD values for masking, it is possible to show the dynamic blood behaviour based on a single MRA image, without the use of contrast agents.

R1 and R2 values of each voxel of a plurality of voxels representing the portion, may be calculated, wherein each voxel of the plurality of voxels corresponds to a volume of the portion. By comparing the R1 and R2 values of each voxel with the known R1 and R2 values of blood, a first group of voxels of the plurality of voxels representing the identified blood vessels may be selected.

That is, the voxel having the R1 and R2 values being equal to the known R1 and R2 values of blood, or falling within the known ranges of R1 and R2 values of blood, is identified as a voxel representing blood in the imaged portion. Consequently, the voxel having the R1 and R2 values being different from the known R1 and R2 values of blood, or falling outside the known ranges of R1 and R2 values of blood, is identified as a voxel representing non-blood tissues in the imaged portion Then, based on the known R1 and R2 values of blood, it is possible to identify the blood vessels of the portion by identifying the blood of the portion.

Additionally, or in combination, based on the known R1 and R2 values of blood of arteries, of blood of early inflow arteries, of blood of late inflow arteries, and of blood of veins, the arteries, the early inflow arteries, the late inflow arteries, and the veins, may be respectively identified.

The quantification values for each voxel, including the R1, R2 and even PD, may be calculated in different known ways. For example, the R1 and R2 values may be calculated by generating R1 and R2 maps, respectively. When the quantification values comprise additional parameters, e.g., a PD value, additional maps, e.g., a PD map, may be generated. The R1, R2 and PD maps describe the signal behaviour of the multi-contrast images resulted from the multi-contrast MR sequence.

At least two multi-contrast images are needed for generating each of the above-mentioned maps. Thus, a plurality of multi-contrast images is needed to generate the R1, R2 and PD maps. It is common that a MR scanner may perform an acquisition and result in a plurality of images with different contrasts. Thus, the step of acquiring the multi-contrast MR sequence and the step of generating the plurality of multi-contrast images may be one step instead of two.

Alternatively, it is possible to recognise blood directly from the raw data, i.e. the multi-contrast MR sequence, without analysing the plurality of multi-contrast images. That is, the identification of the blood may be performed without calculating on the R1, R2 values of the voxels.

It is known that the acquired multi-contrast MR sequence has already defined the characteristics of different tissues, including the blood, in terms of signal behaviours of the plurality of multi-contrast images, e.g., signal intensities in the images. For example, one tissue may have a higher signal intensity (bright) in one image, and it may have a lower signal intensity (dark) in another image. The quantification information, e.g., R1, R2 and PD, is merely an objective description of the signal behaviours in the images. Therefore, it is not necessary to generate the plurality of multi-contrast images and calculate the quantification values for identifying the blood vessels of the portion, as the multi-contrast MR sequence itself simply comprises all the information of the plurality of multi-contrast images. Thus, the predetermined characteristic of blood may comprise: a representation of a signal intensity of blood.

The term "intensity", also known as "signal intensity", in the field of MR refers to a shade of grey of a tissue or of a voxel representing the tissue in an MRI image. Generally, a high intensity means it would look "white" in the MRI image, an intermediate intensity means it would look "grey" in the MRI image, and a low intensity means it would look "black" in the MRI image.

Based on the expected signal intensity of blood, it is possible to select the part of the multi-contrast MR sequence representing the identified blood vessels directly, without analysing the multi-contrast images.

Based on the expected signal intensity of blood of the arteries, of blood of the early inflow arteries, of blood of the late inflow arteries, and of blood of the veins, it is possible to select the part of the multi-contrast MR sequence representing the blood of arteries, the blood of the early inflow arteries, the blood of the late inflow arteries, and the blood of the veins, respectively.

After identifying either voxels representing a part of the blood vessels, or a part of the multi-contrast MR sequence representing the part of the blood vessels, an MRA image frame for visualising the part of the blood vessels of the imaged portion may be generated by known methods.

The identified blood and/or blood vessels can be segmented from the surrounding tissues to generate an MRA image frame depicting mainly the identified blood and/or blood vessels.

Image segmentation is known as a process of partitioning a digital image into multiple segments (e.g., sets of pixels or voxels). A goal of the image segmentation is to simplify the representation of an image such that it becomes more meaningful and/or easier to analyse.

Alternatively, or in combination, the MRA image frame can be generated by a masking step. Masking technique is known for separating a part of an image from its surroundings in the image based on certain criteria.

The masking step may comprise creating a mask which covers a part of the image based on the criteria, and treating this part and its surroundings in the image differently.

For example, the values of the relaxation rates R1 and R2 can be used as criteria to separate the first part of the identified blood vessels from its surrounding tissues. Then the selected second group of voxels may be "masked" and treated differently from other voxels.

The masked voxels and the unmasked voxels can be treated differently in different ways, such as changing the brightness and/or the colour of the voxels. For example, the MRA image frame may be generated by keeping the brightness of the masked voxels unchanged, while suppressing the brightness of the other voxels. Alternatively, the MRA image frame may be generated by increasing the brightness of the masked voxels, while keeping the brightness of the other voxels unchanged.

Different MRA image frames for respectively visualising different parts of the blood vessels of the imaged portion, e.g., the arteries, the early inflow arteries, the late inflow arteries, and the veins, may be generated.

The dynamic MRA image may be generated based on a plurality of MRA image frames in different ways. In order to generate a dynamic MRA image, a minimum number of the MRA image frames is two. A lager number of MRA image frames can better visualise the dynamic characters of the blood flow. For example, a serial of MRA image frames each covering a small part of the identified blood vessels may be generated. The visualisation of the dynamic blood flow may be achieved by displaying a rapid succession of the serial of MRA image frames. By consecutively displaying the serial of MRA image frames, the dynamic MRA image may appear as a dynamic image, or as a short video clip, to visualise the dynamic blood flow within the identified blood vessels. This may facilitate the analysis of the blood vessels.

Each voxel of the plurality of voxels may have an intensity value. The method may comprise a step of calculating a perfusion value by summing the intensity value of each voxel of the voxels representing the identified blood or blood vessels.

A perfusion is known as a delivery of blood to a capillary system in a tissue. The perfusion is normally measured as a rate at which the blood is delivered to the tissue at a unit of $m^3/(s \cdot kg)$. Thus, the perfusion is important for assessing a patient's condition, e.g., in case of strokes, plaques or vessel constrictions.

The sum of the intensities of the voxels representing the identified blood vessels is proportional to a total amount of blood that entered the imaged portion during acquisition. Thus, the sum of the intensities, i.e. the calculated perfusion value, may be considered as a measure for perfusion of the patient. The higher the calculated perfusion value, the higher the perfusion. The lower the calculated perfusion value, the lower the perfusion.

It is advantageous to provide an estimation of the perfusion based on the multi-contrast MR sequence.

The method may comprise steps of calculating a first sum by summing intensity values of voxels of the plurality of voxels representing the first part of the identified blood vessels; calculating a second sum by summing intensity values of voxels of the plurality of voxels representing the second part of the identified blood vessels; and calculating a rate of change of the first sum and second sum as a measure of a mean transit time of blood through the portion of the body.

Mean Transit Time (MU) of blood is known as an average time, normally in seconds, that the blood spends within a determinate volume of capillary circulation.

Since the sum of the intensities of a part of the identified blood vessels is proportional to a total amount of blood that entered this part, a rate of change of the sums over the different parts of the blood vessels may indicate how fast the blood enters and/or leaves the imaged portion. Thus, the rate of change of the sums may be considered to be proportional to the mean transit time. The faster the sum increases, the shorter the mean transit time. The slower the sum increases, the longer the mean transit time.

It is advantageous to provide an estimation of the mean transit time based on the multi-contrast MR sequence.

In connection with FIGS. 2a-6c, different examples of dynamic MRA images will be discussed in more detail.

In the examples of FIGS. 2a-6c, the identified blood vessels or a part of the identified blood vessels are visualised by a Maximum Intensity Projection, MIP.

MIP is a method for visualising 3D data that projects in a visualisation plane the voxels with a maximum intensity. In other words, the MIP projection lines are projected over a plane through a portion of a body, and the maximum intensity of each projection line is identified and visualised.

Alternatively, Minimum Intensity Projection (MinIP) is a method for visualising 3D data that projects in a visualisation plane the voxels with a minimum intensity. Consequently, MinIP imaging can visualise structures with a low intensity in an imaged volume. In other words, the MinIP projection lines are projected over a plane through a portion of a body, and the minimum intensity of each projection line is identified and visualised. MinIP imaging is commonly used to diagnose lung related diseases.

For example, MIP or MinIP projection lines may be projected over an axial plane through a portion of a body, and the maximum intensity of each projection line is identified and visualised. An array of maximum or minimum values forms one row in a sagittal image. After repeating the procedure for all rows, the final sagittal image may be constructed. That is, the maximum or minimum intensities form the final sagittal image of the imaged portion.

Even though an MRA image may visualise 3D slices that contain the entire identified blood vessels of interest, it is more common to display the 3D information on a 2D display, such as a computer monitor, by MIP or MinIP imaging. A 2D image of a selected volume may be generated where each pixel is represented by displaying the maximum or minimum intensity in each voxel.

By MIP imaging, the resulting MRA images resemble conventional catheter angiography images. That is, the identified blood vessels look brighter (e.g., in white colour) and other tissues look darker (e.g., in black colour) in the resulted MRA image.

By MinIP imaging, the resulting MRA images appear as reversed images of the resulting MRA images. That is, the identified blood vessels look darker (e.g., in black colour), and other tissues look brighter (e.g., in white colour) in the resulted MRA image.

A sagittal plane, also known as a longitudinal plane, is an anatomical plane which divides the body or a portion of the body into right and left parts. For example, the sagittal plane may be in the centre of the body and split it into two equal halves, or away from the midline and split it into two unequal parts (para-sagittal).

Alternatively, or in combination, animations can be rendered by several MRA image frames in which the viewpoint is slightly different from one to the other, thus creating the illusion of rotation of the imaged object. This may facilitate the viewer to find the relative 3D positions of the object components. All of the method steps and examples in the application using MIP can be analogously implemented by using MinIP instead.

Figure 2A:
FIG. 2a-2c illustrate three MRA image frames of a dynamic MRA image.
Figure 2B:
Figure 2C:

FIGS. 2a-2c are a set of three MRA image frames of a dynamic MRA image. In FIGS. 2a-2c, the MIP projection lines are set to project from front left to back right of the imaged head and neck, creating a view from front left of the head.

The dynamic MRA image illustrating the MRA image frames of FIGS. 2a-2c may render a dynamic representation of an acquired multi-contrast MR sequence of a head and neck portion of a patient.

FIG. 2a illustrates a first MRA image frame visualising a first part of the blood vessels of the imaged portion. Here, the first part is the early inflow arteries, which are mainly the carotids in the neck.

FIG. 2b illustrates a second MRA image frame visualising a second part of the blood vessels of the imaged portion. Here, the second part is the entire artery area, which include both the carotids in the neck and the circle of Willis in the head.

FIG. 2c illustrates a third MRA image frame visualising a third part of the blood vessels of the imaged portion. Here, the third part is all segmented vessels of the neck and the head, including both arteries and veins.

The dynamic MRA image of FIGS. 2a-2c can visualise a dynamic blood flow, in bright colours, from the blood entering the carotids of the neck, then flowing through the circle of Willis into the entire head, and finally flowing back via the returning veins.

The dynamic MRA image may be constructed based on these three MRA image frames of FIGS. 2a-2c by known techniques. For example, the dynamic MRA image may be generated by consecutively displaying these three MRA image frames of FIGS. 2a-2c.

There are different ways to realise MIP imaging. Instead of projecting MIP projecting lines over the entire imaged portion as for FIGS. 2a-2c, it is possible to projecting MIP projecting lines over one or a few slices of the imaged portion.

Alternatively, the set of three MRA image frames of FIGS. 2a-2c may be visualised by MinIP imaging. Such MRA image frames would look like reverse images of FIGS. 2a-2c. That is, the dynamic MRA image would visualise a dynamic blood flow, in dark colours, from the blood entering the carotids of the neck, then flowing through the circle of Willis into the entire head, and finally flowing back via the returning veins.

FIGS. 3a-3c and FIGS. 4a-4c are two sets of MRA image frames of two dynamic MRA images, of a same multi-contrast MR sequence of a head and neck portion of a patient.

In the examples of FIGS. 3a-3c and FIGS. 4a-4c, MIP imaging are performed for seven neighbouring sagittal slices of a neck and a head, in order to provide seven different views of the same imaged portion from seven slightly different viewpoints.

Figure 3A:
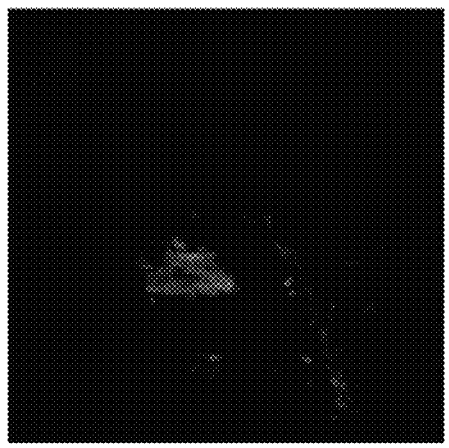
FIG. 3a-3c illustrate three MRA image frames of a dynamic MRA image.
Figure 3B:
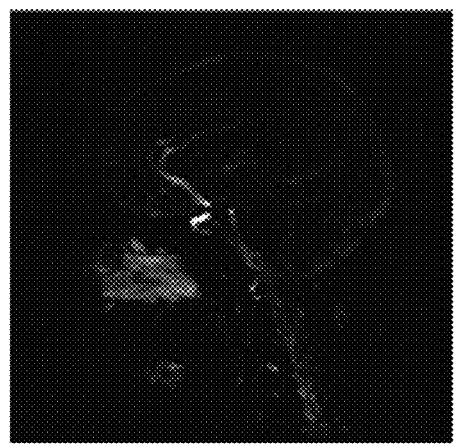
Figure 3C:

For FIGS. 3a-3c, the MIP projection lines are projected over an axial plane through the centre of the head. For FIGS. 4a-4c, the MIP projection lines are projected over an axial plane 4 cm off-centre of the head. Thus, the viewpoints of these two dynamic MRA images are slightly different.

Figure 4A:
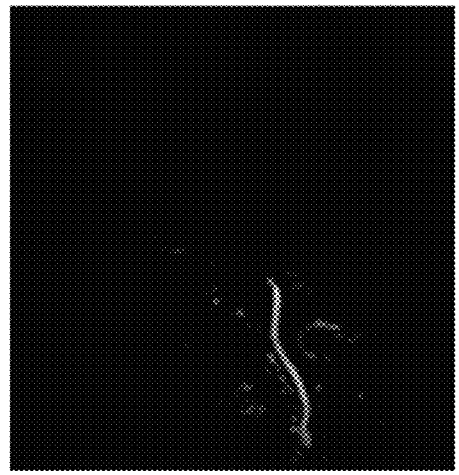
FIG. 4a-4c illustrate three MRA image frames of a dynamic MRA image.

FIG. 3a and FIG. 4a illustrate MRA image frames visualising a first part of the blood vessels of the imaged portion. Here, the first part is the early inflow arteries, which are mainly the carotids in the neck.

Figure 4B:
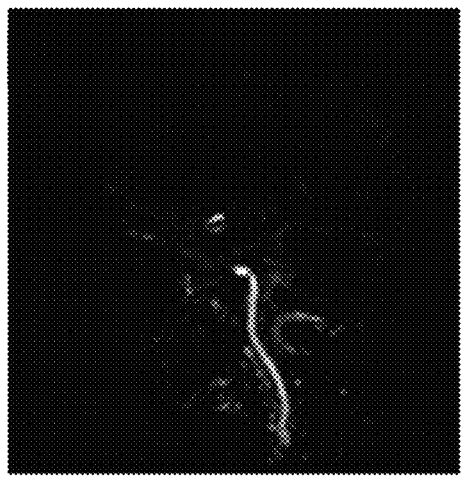

FIG. 3b and FIG. 4b illustrate MRA image frames visualising a second part of the blood vessels of the imaged portion. Here, the second part is the entire artery area, which include both the carotids in the neck and the circle of Willis in the head.

Figure 4C:

FIG. 3c and FIG. 4c illustrate MRA image frames visualising a third part of the blood vessels of the imaged portion. Here, the third part is all segmented vessels of the neck and the head, including both arteries and veins.

Besides the viewpoints, the examples of FIGS. 3a-3c and FIGS. 4a-4c differ from the examples of FIGS. 2a-2c in that the voxels representing the visualised first, second and third part of the blood vessels in FIGS. 3a-3c and FIGS. 4a-4c, respectively, are displayed with an increased brightness. That is, the second part in FIG. 3b is brighter than the first part in FIG. 3a, and the third part in FIG. 3c is brighter than the second part in FIG. 3b. The dynamic features of the blood may be visualised as a transition of brightness.

Alternatively, or in combination, the different parts of the blood vessels may be displayed in different colours, such that the dynamic features of blood may be visualised as a transition of colours. For example, all the arteries can be coloured red, all the veins can be coloured blue.

The dynamic MRA images of FIGS. 3a-3c and FIGS. 4a-4c may respectively visualise a dynamic blood flow, in bright colours, from the blood entering the carotids of the neck, then flowing through the circle of Willis into the entire head, and finally flowing back via the returning veins. However, the dynamic MRA images of FIGS. 3a-3c and FIGS. 4a-4c may visualise the dynamic blood flow from two different viewpoints, in order to facilitate the analysis.

Alternatively, the examples of FIGS. 3a-3c and FIGS. 4a-4c may be visualised by MinIP imaging. Such MRA image frames would look like reverse images of FIGS. 3a-3c and FIGS. 4a-4c. That is, the dynamic MRA image would visualise a dynamic blood flow, in dark colours, from the blood entering the carotids of the neck, then flowing through the circle of Willis into the entire head, and finally flowing back via the returning veins. There are different ways to visualising MRA images. In the examples of FIGS. 5a-6c, a method different from the examples of FIGS. 2a-4c will be discussed in more detail.

FIGS. 5a-5c and FIGS. 6a-6c are two sets of MRA image frames of two dynamic MRA images, of a same multi-contrast MR sequence of a head and neck portion of a patient.

Figure 5A:
FIG. 5a-5c illustrate three MRA image frames of a dynamic MRA image.
Figure 5B:
Figure 5C:
Figure 6A:
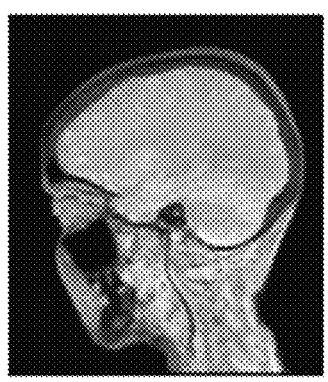
FIG. 6a-6c illustrate three MRA image frames of a dynamic MRA image.
Figure 6B:
Figure 6C:

Similar to the examples of FIGS. 3a-3c and FIGS. 4a-4c, MIP imaging in the example of FIGS. 5a-5c and FIGS. 6a-6c are performed for seven neighbouring sagittal slices of a neck and a head, in order to provide seven different views of the same imaged portion from seven slightly different viewpoints. For FIGS. 5a-5c, the MIP projection lines are projected over an axial plane through the centre of the head. For FIGS. 6a-6c, the MIP projection lines are projected over an axial plane 4 cm off-centre of the head. Thus, the viewpoints of these two dynamic MRA images of 5a-5c and FIGS. 6a-6c are slightly different.The examples of FIGS. 2a-4c are similar to conventional catheter angiography images. That is, the identified blood vessels look brighter (e.g., in white colour) and other tissues look darker (e.g., in black colour) in the MRA images. However, the examples of FIGS. 5a-5c and FIGS. 6a-6c are provided with a static background image illustrating the whole imaged portion, i.e. the head and the neck in the examples of FIGS. 5a-5c and FIGS. 6a-6c.

In FIGS. 5a-5c and FIGS. 6a-6c, the static background image is a synthetic T1 weighted (T1W) image. The static background image may also be a synthetic T2 relaxation time weighted, T2W, a PD weighted image, or any other types of synthetic MR images illustrating the imaged portion.

The synthetic MR image (static background image) may be generated based on the multi-contrast MR sequence. For example, the synthetic MR image may be generated based on the R1, R2 and PD values of the voxels. The concept of synthetic MR imaging is well-known in the field, see e.g. "Cerebral Magnetic Resonance Image Synthesis", Bobman et al. *Am J NeuroRadiol* 1985; 6:265-269.

FIG. 5a and FIG. 6a illustrate MRA image frames visualising a first part of the blood vessels of the imaged portion. Here, the first part is the early inflow arteries, which are mainly the carotids in the neck.

FIG. 5b and FIG. 6b illustrate MRA image frames visualising a second part of the blood vessels of the imaged portion. Here, the second part is the entire artery area, which include both the carotids in the neck and the circle of Willis in the head.

FIG. 5c and FIG. 6c illustrate MRA image frames visualising a third part of the blood vessels of the imaged portion. Here, the third part is all segmented vessels of the neck and the head, including both arteries and veins.

In the examples of FIGS. 5a-5c and FIGS. 6a-6c, the visualised part of the blood vessels is "subtracted" from the static background image. That is, different from those "bright" blood vessels in FIGS. 2a-4c, the visualized blood vessels are "dark" in FIGS. 5a-6c.

For example, the dynamic MRA images in the examples of FIGS. 2a-2c, may be "subtracted" from a background image generated based on the same multi-contrast MR sequence used for generating the dynamic MRA images. This may result in three MRA image frames having the blood vessels in dark colours within the whole imaged portion in bright colours.

"Subtracting" one image from another image may be performed in different ways. For example, it may refer to subtracting each voxel of one image from its corresponding voxel of another image. "Subtracting" a first voxel from a second voxel may refer to subtracting a signal intensity of the first voxel from the signal intensity of the second voxel.

The MRA images frames of FIGS. 5a-5c and FIGS. 6a-6c look alike images produced during Susceptibility Weighted Imaging (SWI). For SWI a single T1W image is acquired where all blood vessels are dark. The contrast in this image is enhanced by multiplication of the associated phase image and making a Minimum Intensity Projection over a limited number of neighbouring slices. However, it is impossible to visualise dynamic behaviours of the blood by SWI.

The voxels representing the visualised first, second and third part of the blood vessels in FIGS. 5a-5c and FIGS. 6a-6c, respectively, are displayed with a reduced brightness. That is, the second part in FIG. 5b is darker than the first part in FIG. 5a, and the third part in FIG. 5c is brighter than the second part in FIG. 5b. The dynamic features of the blood may be visualised as a transition of darkness, i.e. the visualised blood vessels are getting darker and darker in the dynamic MRA image.

Instead of "subtracting" the visualised part of the blood vessels from the static background image, a similar effect of the examples of FIGS. 5a-5c and FIGS. 6a-6c can be achieved by MinIP imaging. That is, the dynamic MRA image would visualise a dynamic blood flow, in dark colours, from the blood entering the carotids of the neck, then flowing through the circle of Willis into the entire head, and finally flowing back via the returning veins. Since the tissues around the blood vessels are visible, analysing the blood vessels, e.g., the size and the relative position, may be facilitated. The different parts of the blood vessels of the different MRA image frames may be at least partially overlapping. Alternatively, they may be not overlapping at all.

The imaged portion used in the examples comprises a head and/or a neck. However, the imaged portion may comprise different portions of a human or an animal, e.g., a heart, a chest, an abdomen, a pelvis, even the whole body.

The invention claimed is:

1. A dynamic magnetic resonance angiography, MRA, method, comprising:
   acquiring, by an MR scanning device, a multi-contrast magnetic resonance, MR, sequence of a portion of a body, through a single multi-contrast MR acquisition, without administering a contrast agent to the body;
   wherein the multi-contrast MR sequence comprises quantification information of the portion;
   wherein the quantification information of the portion comprises a longitudinal relaxation rate R1, and a transverse relaxation rate R2;
   identifying, by a processing circuit, blood vessels of the portion by identifying blood of the portion by comparing predetermined characteristic of blood with the quantification information of the portion;
   wherein the predetermined characteristic of blood comprises: a value of a longitudinal relaxation rate R1 of blood, and a value of a transverse relaxation rate R2 of blood;
   generating, by the processing circuit, a first MRA image frame and a second MRA image frame, based on the multi-contrast MR sequence, respectively visualising a first part and a second part of the identified blood vessels;
   generating, by the processing circuit, a dynamic MRA image for visualising a dynamic blood flow through a part of the portion, based on the first and second MRA image frame;
   generating a plurality of multi-contrast images based on the multi-contrast MR sequence; and
   identifying the blood vessels of the portion by identifying the blood of the portion based on the predetermined characteristic of blood and the plurality of multi-contrast images,
   wherein the step of identifying blood vessels comprises:
   calculating quantification values of each voxel of a plurality of voxels representing the portion, based on the plurality of multi-contrast images;
   wherein each voxel of the plurality of voxels corresponds to a volume of the portion, and
   wherein the quantification values comprise: a value of a longitudinal relaxation rate R1 and a value of a transverse relaxation rate R2;
   selecting a first group of voxels of the plurality of voxels representing the identified blood vessels, by comparing the quantification values of each voxel with the predetermined characteristic of blood.

2. The method of claim 1, wherein the step of generating a first MRA image frame comprises:

determining a first group of values corresponding to the first part of the identified blood vessel to be visualised in the first MRA image frame,
wherein the first group of values comprise a value of longitudinal relaxation rate R1 and a value of transverse relaxation rate R2;
selecting a second group of voxels of the plurality of voxels representing the first part of the identified blood vessel by comparing the quantification values of each voxel with the first groups of values;
generating the first MRA image frame visualising the first part of the identified blood vessels, based on the second group of voxels.

3. The method of claim 1, wherein the quantification information of the portion comprises a Proton Density, PD; wherein the predetermined characteristic of blood comprises: a value of a PD of blood.

4. The method of claim 3, wherein the quantification values of each voxel comprise: a value of a PD.

5. The method of claim 4, wherein the first group of values comprise: a value of a PD.

6. The method of claim 1, wherein the step of identifying blood vessels comprises:
selecting a part of the multi-contrast MR sequence representing the identified blood vessels, based on the predetermined characteristic of blood;
wherein the predetermined characteristic of blood comprises: a representation of a signal intensity of blood.

7. The method of claim 6, wherein the step of generating a first MRA image frame comprises:
selecting a first group of data of the selected part of the multi-contrast MR sequence corresponding to the first part of the identified blood vessel;
generating the first MRA image frame visualising the first part of the identified blood vessels, based on the multi-contrast MR sequence and the first group of data.

8. The method of claim 1, wherein the step of generating a first and a second MRA image frame comprises:
visualising the first MRA image frame and the second MRA image frame, by a Maximum Intensity Projection, MIP.

9. The method of claim 8, wherein the step of generating a first and a second MRA image frame comprises:
generating a synthetic MR image representing the portion based on the multi-contrast MR sequence, as a static background image of the dynamic MRA image;
generating the dynamic MRA image based on the first, the second MRA image frame, and the synthetic MR image.

10. The method of claim 1, wherein the first part and the second part of the identified blood vessels are:
at least partially overlapping, or
nonoverlapping.

11. The method of claim 1, wherein the first part of the identified blood vessels comprises early inflow arteries of the identified blood vessels, and
the second part of the identified blood vessels comprises late inflow arteries of the identified blood vessels.

12. The method of claim 1, wherein the first part of the identified blood vessels comprises arteries of the identified blood vessels.

13. The method of claim 12, wherein the second part of the identified blood vessels comprises all the identified blood vessels, or veins of the identified blood vessels.

14. The method of claim 1, wherein the dynamic MRA image consecutively displays the first and second MRA image frame.

15. The method of claim 14, wherein at least a first portion of the first MRA image frame and a second portion of the second MRA image frame are displayed in different colours or different brightnesses.

16. The method of claim 1, further comprising:
generating at least a third MRA image frame visualising at least a third part of the identified blood vessels;
generating the dynamic MRA image based on the first, second and at least the third MRA image frame,
wherein the first part, second part and at least the third part of the identified blood vessels are:
at least partially overlapping, or
nonoverlapping.

17. The method of claim 1, wherein the value of the longitudinal relaxation rate R1 of blood is in a range of 0.4-0.6 $s^{-1}$; and
the value of transverse relaxation rate R2 of blood is in a range of 20-30 $s^{-1}$.

18. The method of claim 1, wherein the portion of the body comprises a head and/or a neck.

19. The method of claim 1, wherein each voxel of the plurality of voxels has an intensity value,
wherein the method further comprises:
calculating a perfusion value by summing the intensity value of each voxel of the first group of voxels.

20. The method of claim 1, wherein each voxel of the plurality of voxels has an intensity value,
wherein the method further comprises:
calculating a first sum by summing intensity values of voxels of the plurality of voxels representing the first part of the identified blood vessels;
calculating a second sum by summing intensity values of voxels of the plurality of voxels representing the second part of the identified blood vessels;
calculating a rate of change of the first sum and second sum as a measure of a mean transit time of blood through the portion of the body.

21. The method of claim 1, wherein the step of generating a first and a second MRA image frame comprises:
visualising the first MRA image frame and the second MRA image frame, by a Minimum Intensity Projection, MinIP.

22. A non-transitory computer readable recording medium having computer readable program code recorded thereon which when executed on a device having processing capability is configured to perform the method of claim 1.

23. A dynamic magnetic resonance angiography, MRA, system, comprising:
an MR scanning device configured to:
acquire a multi-contrast magnetic resonance, MR, sequence of a portion of a body, through a single multi-contrast MR acquisition;
wherein the multi-contrast MR sequence comprises quantification information of the portion;
wherein the quantification information of the portion comprises a longitudinal relaxation rate R1, and a transverse relaxation rate R2;
a processing circuit configured to:
identify blood vessels of the portion by identifying blood of the portion by comparing predetermined characteristic of blood with the quantification information of the portion;
wherein the predetermined characteristic of blood comprises: a value of a longitudinal relaxation rate R1 of blood, and a value of a transverse relaxation rate R2 of blood;

generate a first MRA image frame and a second MRA image frame, based on the multi-contrast MR sequence, respectively visualising a first part and a second part of the identified blood vessels;

generate a dynamic MRA image for visualising a dynamic blood flow through a part of the portion, based on the first and second MRA image frame;

generate a plurality of multi-contrast images based on the multi-contrast MR sequence; and identify the blood vessels of the portion by identifying the blood of the portion based on the predetermined characteristic of blood and the plurality of multi-contrast images, wherein the processing circuit is further configured to:

calculate quantification values of each voxel of a plurality of voxels representing the portion, based on the plurality of multi-contrast images;

wherein each voxel of the plurality of voxels corresponds to a volume of the portion, and wherein the quantification values comprise: a value of a longitudinal relaxation rate $R_1$ and a value of a transverse relaxation rate $R_2$; and select a first group of voxels of the plurality of voxels representing the identified blood vessels, by comparing the quantification values of each voxel with the predetermined characteristic of blood.

24. The system as claimed in claim 23, further comprising:

a user interface configured to display the dynamic MRA image.

* * * * *